(12) United States Patent
Engman

(10) Patent No.: US 6,174,317 B1
(45) Date of Patent: Jan. 16, 2001

(54) TOOL FOR USE AT LAPAROSCOPIC SURGERY AT UTERUS

(75) Inventor: Mikael Engman, Södertälje (SE)

(73) Assignee: Endolink AB, Södertälje (SE)

( * ) Notice: Under 35 U.S.C. 154(b), the term of this patent shall be extended for 0 days.

(21) Appl. No.: 09/147,823

(22) PCT Filed: Sep. 16, 1997

(86) PCT No.: PCT/SE97/01565
  § 371 Date: Mar. 15, 1999
  § 102(e) Date: Mar. 15, 1999

(87) PCT Pub. No.: WO98/10707
  PCT Pub. Date: Mar. 19, 1998

(30) Foreign Application Priority Data

Sep. 16, 1996 (SE) .................................................. 9603363

(51) Int. Cl.[7] .................................................. A61B 17/42
(52) U.S. Cl. .................................................. 606/119
(58) Field of Search .................................. 606/119, 120, 606/121, 122, 123, 124, 125, 126; 604/164, 165

(56) References Cited

U.S. PATENT DOCUMENTS

| | | | |
|---|---|---|---|
| 3,877,433 | * 4/1975 | Librach | 606/119 |
| 4,000,743 | * 1/1977 | Weaver | 606/119 |
| 4,807,625 | * 2/1989 | Singleton | 606/125 |
| 5,147,316 | * 9/1992 | Castillenti | 604/164 |
| 5,209,754 | 5/1993 | Ahluwalia | 606/119 |
| 5,217,466 | 6/1993 | Hasson | 606/119 |
| 5,380,291 | * 1/1995 | Kaali | 604/164 |
| 5,397,325 | * 3/1995 | Della Badia et al. | 606/144 |
| 5,472,419 | * 12/1995 | Bacich | 606/55 |
| 5,501,691 | * 3/1996 | Goldrath | 606/148 |
| 5,520,698 | 5/1996 | Koh | 606/119 |
| 5,520,702 | * 5/1996 | Sauer et al. | 606/144 |
| 5,562,679 | * 10/1996 | Valtchev | 606/119 |
| 5,591,177 | * 1/1997 | Lehrer | 606/139 |
| 5,800,398 | * 9/1998 | Hahnle et al. | 604/164 |
| 5,836,913 | * 11/1998 | Orth et al. | 602/107 |
| 5,840,077 | * 11/1998 | Rowden et al. | 606/112 |

FOREIGN PATENT DOCUMENTS

94/10926    5/1994  (WO) .

* cited by examiner

Primary Examiner—Paul J. Hirsch
Assistant Examiner—Michael B. Priddy
(74) Attorney, Agent, or Firm—Jacobson, Price, Holman & Stern, PLLC

(57) ABSTRACT

An instrument for use in uterine laparoscopic surgery, said instrument including a tubular element which is adapted for insertion into the vagina with the front end-part of the instrument, as seen in the insertion direction, receiving the cervix, wherewith the edge of the front part of said tubular element is shaped to support against the top wall of the vagina, and wherewith the instrument includes a sealing ring which embraces the tubular element and functions to provide a seal between said element and said vaginal wall. The edge portion of the front part of the tubular element is constructed so that the top wall of the vagina will be supported around the full periphery of said edge portion when the tubular element is positioned in the vagina. The instrument includes end closure means detachably fastened to the tubular element and the rear end-part of the tubular element is adapted to provide an anchorage for a suture which is anchored through the cervix. The rear end of the tubular element, as seen in the insertion direction, carries the end closure means which functions to pressure-seal the passageway passing through said tubular element.

19 Claims, 4 Drawing Sheets

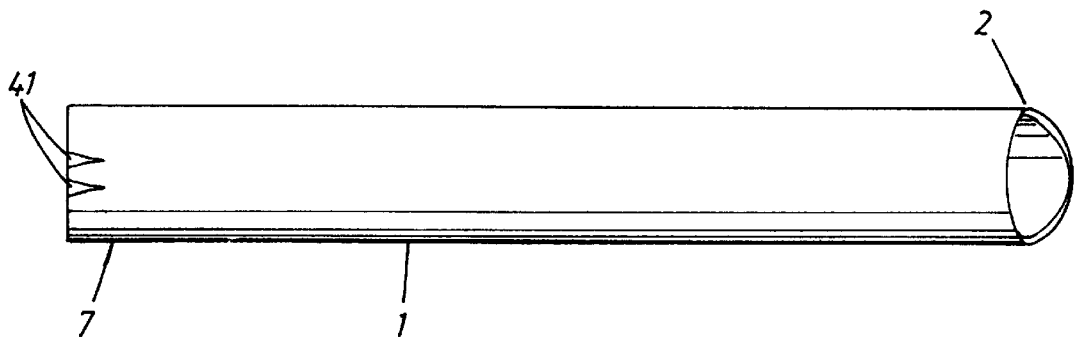
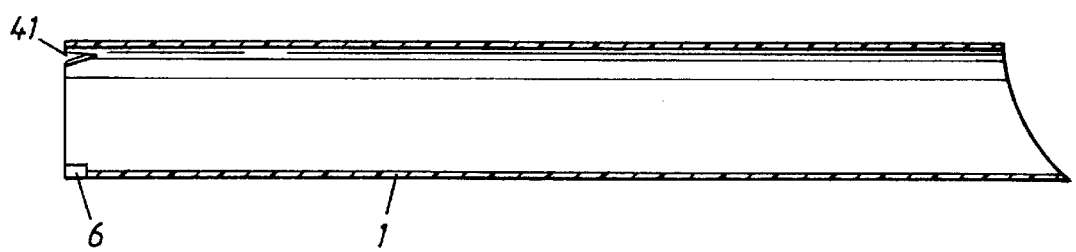
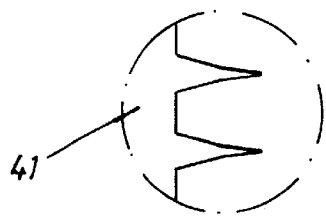

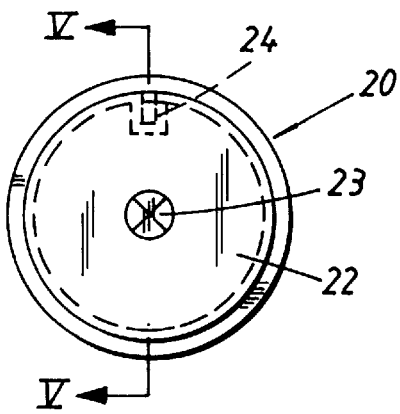
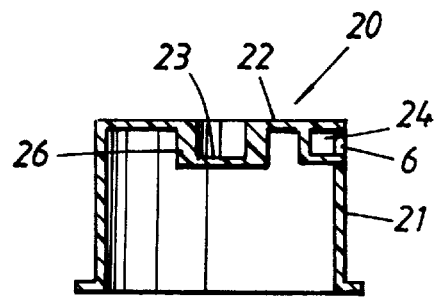
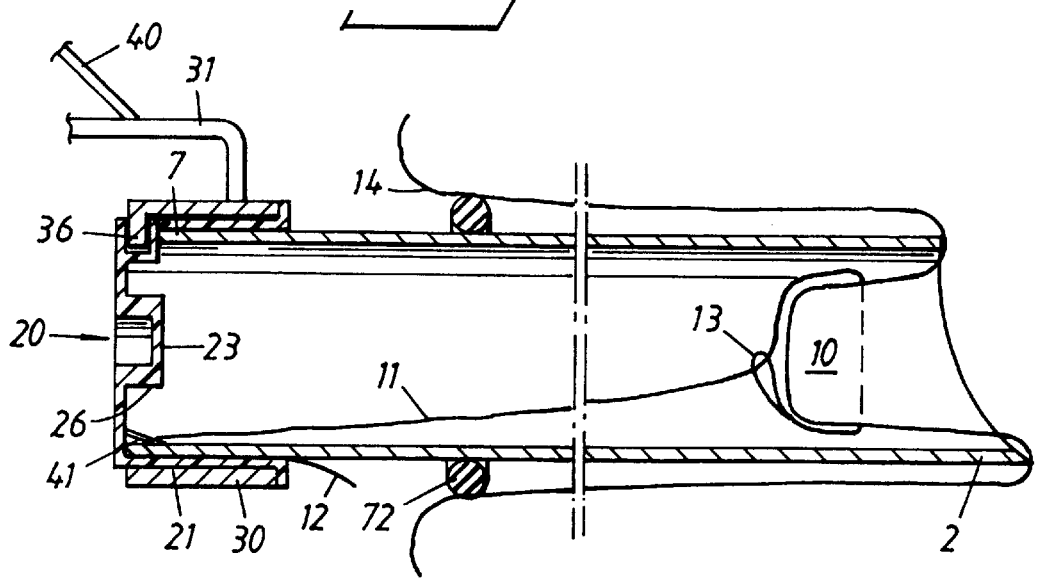

TOOL FOR USE AT LAPAROSCOPIC SURGERY AT UTERUS

BACKGROUND

1. Field of the Invention

The present invention relates to an instrument for laparoscopic uterine surgery of the kind having a tubular element which is adapted for insertion into the vagina with the front end-part of the instrument, as seen in the insertion direction, receiving the cervix, the edge of the front part of the tubular element being shaped to support against the top wall of the vagina, and the instrument including a sealing ring which embraces the tubular element and functions to provide a seal between the element and the vaginal wall.

2. Description of the Related Art

It is known in the performance of an hysterectomy to use a tubular element which is inserted into the vagina such as to bear against the cervix, wherewith the front part of the tubular element supports against the top wall of the vagina so as to raise and support the same, e.g. in the manner of a "pitched tent"; cf WO 94/10926 for instance. A probe is passed through the tubular element, through the neck of the uterus and into the body of the uterus. The probe has an external thread by means of which it can be screwed firmly to the neck of the uterus, or cervix.

One drawback with this known instrument is that the probe blocks the cervical canal.

Another drawback with this known instrument is that it fails to adequately protect the vaginal wall in the case of certain types of surgery.

SUMMARY OF THE INVENTION

One object of the present invention is to provide an instrument which will eliminate these drawbacks either completely or partially.

This object is achieved with an instrument for use in uterine laparoscopic surgery including a tubular element for insertion into the vagina with the front end-part of the instrument, as seen in the insertion direction, receiving the cervix, wherewith the edge of the front part of said tubular element is shaped to support against the top wall of the vagina, and wherewith the instrument includes a sealing ring which embraces the tubular element and functions to provide a seal between the element and the vaginal wall, the edge portion of the front part (2) of the tubular element having a curvature by which the top wall of the vagina is supported around the full periphery of said edge portion when the tubular element is positioned in the vagina, the instrument including end closure means detachably fastened to the tubular element, the rear end-part of the tubular element having anchorage means for a suture which is anchored through the cervix, and the rear end of the tubular element, as seen in the insertion direction, carrying the end closure means which functions to pressure-seal the passageway passing through the tubular element.

Further developments of the instrument include an instrument in which the rear end-part of the tubular element includes a wedge-shaped slit in which a suture can be anchored. The edge portion of the tubular element is defined by a section between the tubular element and a single-curved surface whose concave side lies distal from the tubular element, wherein the generatrix of the single-curved surface is perpendicular to the axis of the tubular element, and wherein a plane which approximates the single-curved surface and which extends parallel with said generatrix defines an angle of roughly 30° with a plane extending normal to the axis of the tubular element. The end closure means may further comprise a central, self-sealing lead-through which is adapted to enable a rod-shaped element to be inserted sealingly into the interior of the tubular element. The end closure means may further include a tubular flange which embraces the rear end-part of the tubular element, and a clamping sleeve which includes a manipulator grip may be firmly clamped on the rear end-part of the tubular element, preferably on the tubular flange of the end closure means. The clamping sleeve can include a rod which can be connected to an external attachment point. The instrument may be further characterized in that the self-sealing lead-through in the end closure means is provided at the bottom of a recess that extends towards the interior of the tubular element, the recess having an undercut part such that a plug can be inserted into the recess and an enlarged peripheral part of the plug snaps into the undercut part, the plug having a through-passing passageway which is aligned with the self-sealing lead-through, therewith enabling a rod-shaped element to be gripped in the passageway in the plug and fixated axially in the plug when the plug is pressed into the recess. The plug may further include a lateral opening for enabling a rod-shaped element to be inserted laterally into and removed laterally from the passageway in the plug when the plug is located outside the recess. The plug and/or the wall of the recess may be comprised of a rubber elastic material, and an insertion end of the plug may be conical, the bottom part of the recess also being conical and having a slightly larger cone angle than the plug insertion end, wherein the cone-apex part of the plug is being compressed more pronouncedly circumferentially around a rod-shaped element in said plug passageway in coaction with the bottom part of the recess wall. Such a plug is adapted to prevent axial leakage of fluid between the rod-shaped element and the recess wall, in coaction with the wall of the recess.

The inventive instrument also enables novel surgical techniques to be carried out, as made evident below.

One important feature of the inventive instrument is that it enables a suture to be fastened in the cervix, and that the tubular element is provided with suture anchoring means, for instance a wedging slot, in the rear, outer end of the element. The instrument thus provides two important functions. Firstly, the forward, inner end of the tubular element can be readily given a chosen "pitching" effect irrespective of the length of the cervix, simply by pulling on the suture until the end of the tube is brought into firm engagement with the upper wall of the vagina with a suitable force, and secondly the cervical canal will not be blocked by an anchoring device. This latter function makes possible an antegrade excision of the cervical canal. It will be understood that by "pitching function" as used in this document is meant a raising and supporting function in a manner similar to that of "pitching" a tent.

A further important feature of the invention is that the front edge of the tubular element is shaped to lie stably against the upper vagina wall around the whole of the cervix. This enables the top of the vagina to be twisted, angled and displaced with the aid of the tubular element.

Because the wall of the tubular element also protects the vagina wall from its top and around its periphery, an antegrade excision can be performed without risk of the excision instrument, for instance a tubular knife, damaging the vagina wall. The instrument is intended primarily for laparoscopic surgery (keyhole surgery).

The inventive contouring of the front end-part of the tubular element enables the top of the vagina to be held raised effectively in the abdominal cavity of the patient, so that it will be distanced far from the bladder and ureters and therewith reduce the risk of damage to these organs.

The inventive contouring of the front, distal end of the tubular element enables the lateral fornices to be lifted high in the uterine canal. This increases the distance to the ureters in relation to the uterine vessel. Good orientation is obtained relative to the forward edge of the tubular element around the full circumference and to the sides. Coagulation and ligature of uterine vessels can be made while using the edge of the tubular element as a reference. At the same time, an indication is given that the instrument is distanced as far as possible from the ureters.

The inventive tubular element includes a passageway that extends along the full length of the element, and the rear end of said element includes a pressure-tight lead-through or transit for the insertion of a rod-like instrument. The ability of the inventive instrument to fixate a holding suture enables supracervical hysterectomy to be performed on the cervical canal, due to the fact that the cervical canal will not be blocked by the suture. It is possible to saw out the cervical canal in an antegrad direction with morcellator, through the medium of a guide inserted into the cervix and with the vaginal wall protected by the tubular element. It will be noted in particular that the inventive instrument permits the use of a probe which is inserted externally through the tubular element and the cervical canal in a pressure-tight fashion and into the body of the uterus, wherewith the probe can then be removed so as to provide surgical access to the cervical canal while holding the cervix stretched against the front edge of the tubular element with the aid of the suture.

According to one particular embodiment, there is provided a readily handled fixation device that enables the position of an elongated element, such as a gripping tool or a probe extending through a lead-through or transit opening of a longitudinally extending closure means to be fixed.

The tubular element can be pressed into the free abdominal cavity by making an incision through the vagina wall, therewith enabling a gripping instrument to be inserted through the closure cap and draw down the morcellate in relatively large pieces into the tubular element, which therewith forms some kind of collecting vessel.

In addition to the cap, the enclosure means may also include a cylindrical flange or sleeve whose one end is shielded or screened by the cap. The sleeve is fitted over the outer end-part of the tubular element. A clamping sleeve may also be fitted over and around the cylindrical closure sleeve, so as to clamp the sleeve firmly and stably against the tubular element. The clamping sleeve may be provided with a handle that facilitates manipulation of the tubular element. The clamping sleeve may also be provided with a rod that enables the tubular element to be fixed at an external fixed point.

The invention will now be described with reference to exemplifying embodiments thereof and also with reference to the accompanying drawings.

BRIEF DESCRIPTION OF THE DRAWINGS

FIG. 1 is a side view of a tubular element forming part of the inventive instrument.

FIG. 2 is an axial sectioned view of the element shown in FIG. 1.

FIG. 3 is an enlarged view of the component 41 in FIG. 1.

FIG. 4 is an end view of a closure fitted over the rear end of the tubular element.

FIG. 5 is a sectional view taken on the line V—V in FIG. 4.

FIG. 6 is a schematic, axial sectioned view of the inventive instrument in one application.

Figure 7:
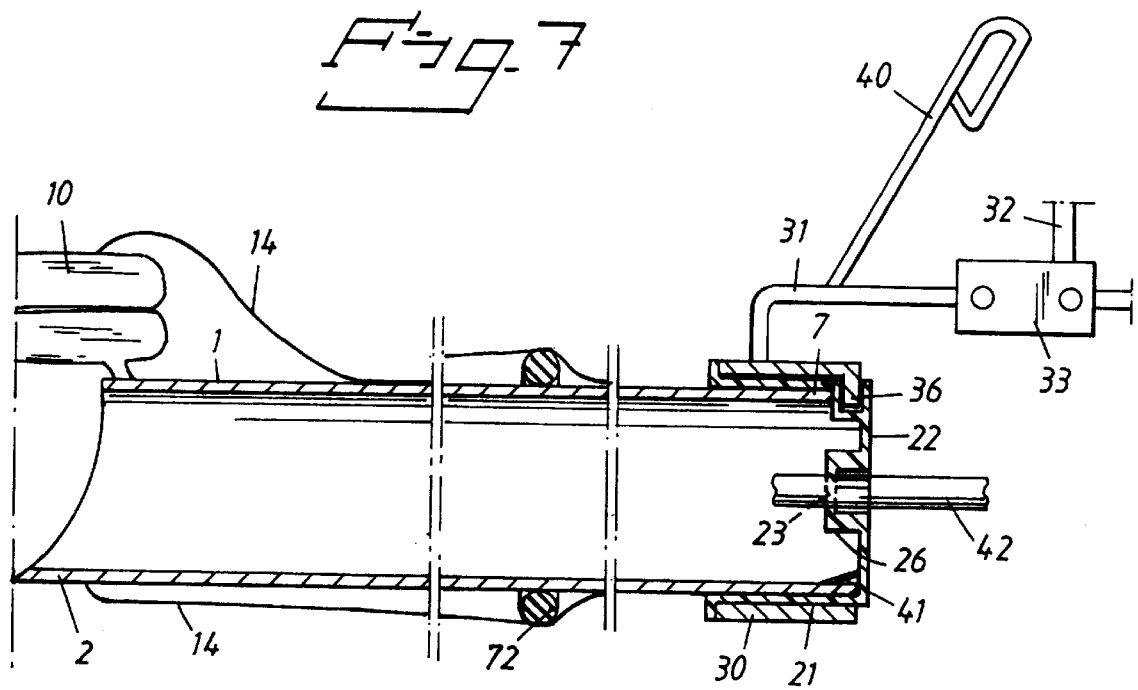
FIG. 7 is an axial sectioned view of the instrument in an alternative application.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE PREFERRED EMBODIMENT

The tubular element 1 shown in FIGS. 1 and 2 is intended to be inserted into the vagina of a patient. The front end 2 of the tubular element is bevelled as seen in the direction of insertion. This bevelling can be approximated by a plane that defines an angle of about 30° with the normal plane of the axis of the tubular element. However, the bevelling may have the form of a single curve surface that is slightly concave outwardly. The generatrix of the single-curve bevel is a straight line that defines generally a right angle with the axis of the tubular element. The single-curve surface has a radius of approximately 50 mm, and the tubular element 1 has a diameter of about 36 mm.

The front end-part 2 of the tubular element 1 is hereby adapted to support against the top vaginal wall around the cervix. The rear, outer end of the tubular element has provided therein two notches or slits 41 which narrow towards their inner ends and which function to enable a suture to be anchored by pulling the suture into at least one of the notches.

As will be apparent from FIG. 6, the inner end 2 of the tubular element is intended to support against the wall of the vagina and around the cervix 10 around its full circumference, and that a sealing cap or end closure means 20 is fitted to the outer end 7 of the tubular element. A loop suture 11 extends through the cervix 10 and is thereby anchored in the cervix. The outer end-part 12 of the suture 11 is wedged firmly in an anchoring notch or slit 41. An outer ring-shaped seal 72 embraces the tubular element 1 and seals against the wall of the vagina. The sealing cap or end closure means 20 and the ring-shaped seal 72 provide, together with the tubular element 1, a pressure shield that screens the vagina. This enables overpressure gas present in the abdominal cavity to leak out through the cervix or the top wall of the vagina in the performance of laparoscopic surgery, without risk of decompression to the surroundings.

A manipulator clamping sleeve 30 is fitted over a tubular part 21 of the edge of the cap or end closure means 20.

The sleeve 30 is provided with a radially and inwardly extending pin 36 which engages in a corresponding recess 6 in the end of the tubular element 1. The cap 20 includes in the junction between end-wall 22 and tubular part 21 an inwardly drawn wall-part 24 which is received in the recess 6 and accommodates the pin 36. Conventional clamping devices enable the sleeve 30 to be stably applied. The sleeve includes an arm 31 which extends rearwardly, generally parallel with the axis of the tubular element 1. The arm 31 enables the instrument to be affixed to an external attachment point which in the FIG. 7 embodiment has the form of a frame 32 that includes an attachment device 33 to which the arm 31 can be fastened. An instrument manipulating handle 40 may be attached to the arm 31.

The cap has a central, recessed part whose bottom wall 23 forms a self-sealing lead-through. The self-sealing lead-through may be formed by slits that are biased towards a sealing position. The cap or enclosure 20 is preferably made of an elastomeric material, such as silicone rubber. It will be apparent that the front end-part 2 of the tubular element 1 lies against the top wall of the vagina around the cervix with a force determined by the tension set in the suture 11. It will also be apparent that a seal 72 establishes a seal between the vagina wall 14 and the outer surface of the tubular element 1.

As will be understood, a rod-shaped tool, for instance a probe 42, can be inserted through the self-sealing lead-through formed by the slits 23. The probe can thus be inserted through the cervix and into the body of the uterus. The sutures 11, 13 form no obstacle to the insertion of the probe. The lead-through will self-seal as the probe is withdrawn.

As a result of the illustrated contour of the front end 2 of the tubular element 1, a good "pitching" effect is obtained and the vagina wall will be effectively protected by the tubular element 1. This is particularly advantageous in the case of diathermy treatment via the outer end of the tubular element and in antegrade excision of the cervix canal.

Coagulation and ligature are effected against the front edge of the tubular element 1. Reference to the inner edge of the tubular element can be easily followed. The tubular element 1 is conveniently comprised of a heat-resistant plastic that acts as an electric insulator and heat insulator. The rear parts of the tubular element 1 may be comprised of a somewhat cheaper plastic material, suitably a non-autoclavable material.

By constructing the tubular element 1 for one-time use only, it is ensured that the surgeon will always be given a new tubular element with smooth vagina vucosa contacting surfaces. This is considered beneficial, since an autoclavable tubular element would also obtain sharp surface irregularities in alternation with sharp medical instruments or mono/bipolar HF energy. The risk of infection in this area is thus reduced when using a tubular element constructed for one-time use only.

As will be seen from FIG. 7, the inventive instrument can be inserted into the free abdominal cavity through an incision made in the vagina wall. Morcellate can be drawn into the tubular element 1 in relatively large pieces with the aid of a generally rod-shaped gripping tool 42 that is inserted through the lead-through or transit 23 and grips the morcellate with its front end, as seen in the insertion direction, for drawing the morcellate down into the tubular element 1.

In the embodiments illustrated in FIGS. 6 and 7, the seal between the outside of the tubular element 1 and the wall 14 of the vagina has the form of a general sealing ring 72.

Figure 8:
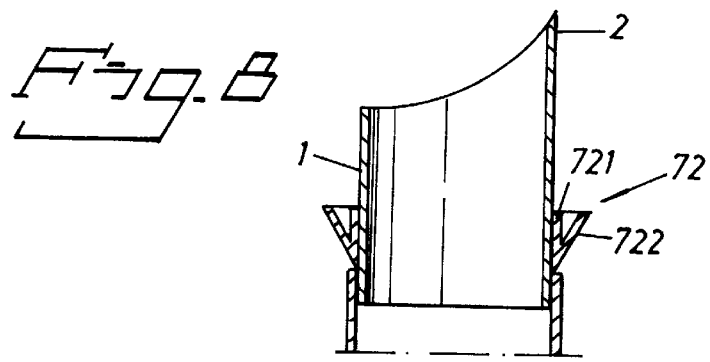
FIG. 8 is an axial sectioned view of a modified form of the tubular element with a special form of outer ring-shaped seal.
Figure 9:
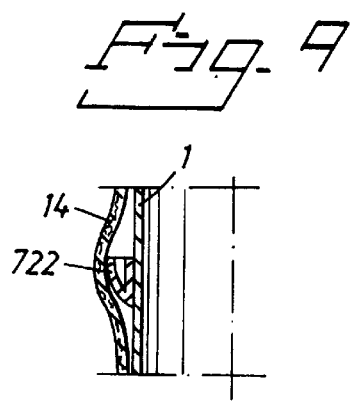
FIGS. 9 and 10 illustrate respectively different states of deformation of the seal shown in FIG. 8.
Figure 10:
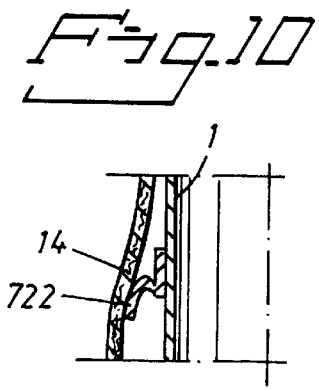

However, it will be obvious that there may be used instead a sealing ring 72 of V-shaped cross-section as shown in FIG. 8, said sealing ring having a cylindrical first leg 721 and a conical second leg 722 and fixed at its radially inner end to one axial end of the cylindrical leg 721. The legs 721 and 722 suitably define therebetween an angle of about 60°. As will be seen from FIG. 8, the leg 722 extends outwardly and forwardly in the insertion direction of the tubular element 1. The seal 22 is comprised suitably of a springy elastic rubber material. As the tubular element 1 with the seal 72 is inserted into the vagina of a patient, the leg 722 will be bent forwards by the forces exerted radially by the vagina wall 14. Thus, the greater the overpressure between the seal 72 and the cervix 10, the stronger the seal provided by the leg 722. It may be difficult in some instances to cause the flange 722 to adopt the configuration shown in FIG. 9, wherewith the flange 722 is bent rearwardly, as shown in FIG. 10, but also in an orientation which is unacceptable to the flange 722, since the flange 722 will then tend to straighten itself. The surgeon, however, will normally be able to urge the flange 722 manually forwards to the position of orientation illustrated in FIGS. 8 and 9.

The leg 722 is made of a rubber elastic material and has a memory shape of the kind illustrated in FIG. 8.

A probe that conveniently has a pointed part bent outwardly through an angle of 40° for instance can be inserted through the cap or enclosure 23 and through the cervix and into the body of the uterus to enable manipulation of the uterus by twisting and/or axial displacement of the instrument. The probe can be inserted through the cervix despite the suture 11 holding the cervix tensioned against the rear end of the tubular element. Naturally, the suture can be clipped-off at any time whatsoever, by means of an appropriate instrument inserted through the self-sealing lead-through 23.

As will be evident from FIG. 5 for instance, the closure means 23 is located in the bottom end of a central, tubular recess in the cap 22.

Figure 11:
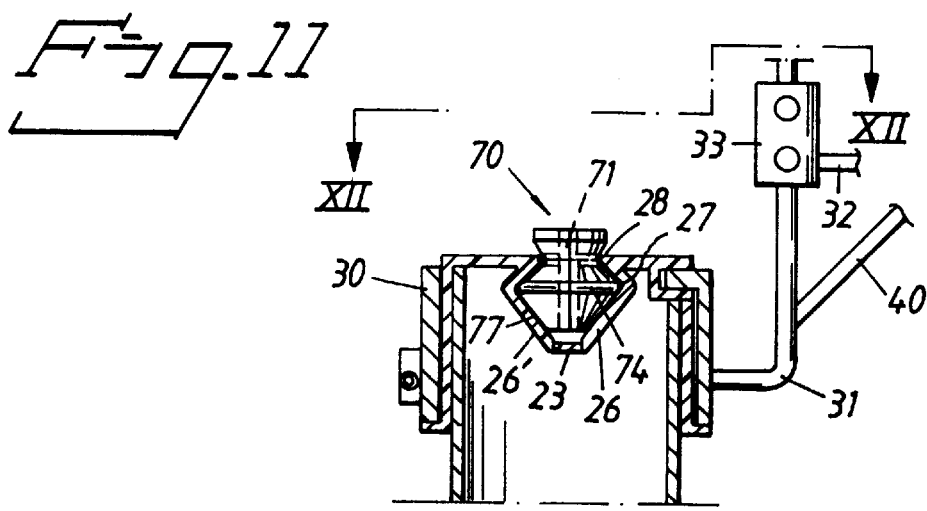
FIG. 11 is a schematic, axially sectioned view of the rear end of the instrument and shows means for fixating a rod-like element axially in the closure.
Figure 12:
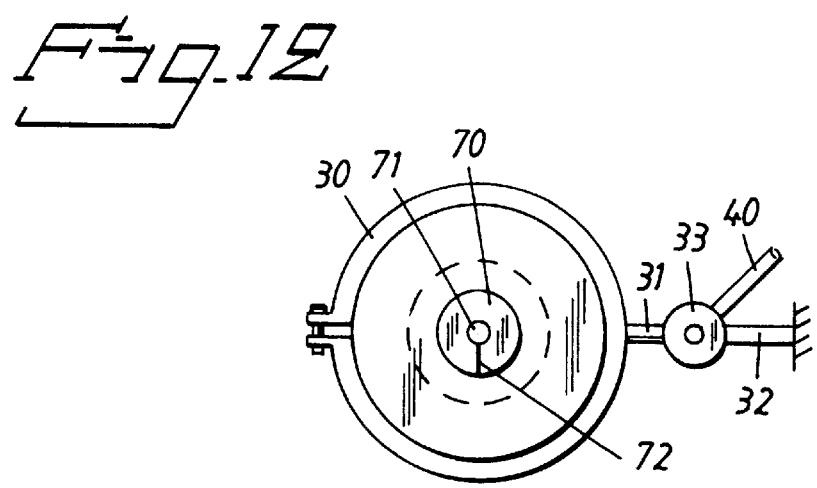
FIG. 12 is a view taken on the line XII—XII in FIG. 11.

In the case of the FIG. 11 embodiment, the central recess 26 includes an undercut part 27. A plug 70 having a waist part 74 can be pressed down in the recess 26 so as to cause the waisted part 74 to snap into the undercut 27. The plug 70 also includes a through-penetrating passageway 71 which lies against and in register with the self-sealing lead-through 23.

Figure 13:
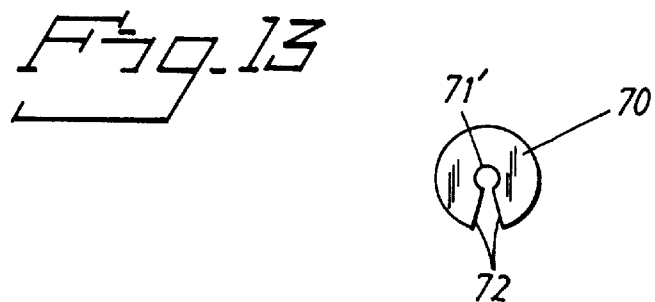
FIG. 13 is a schematic end view of a fixating element.

The plug 70 can be opened to provide lateral access to the passageway 71. In the case of the illustrated embodiment, the plug 70 is comprised of a rubber elastic material which can be considered to be essentially rotationally symmetrical when not subjected to load but which has a sector cut away along an angularly separate axial plane 72 (FIG. 13). When the plug 70 is then compressed circumferentially, the cut surfaces 72 will come into contact with each other and the outer periphery of the plug 70 will be so small as to enable the plug 70 to be pressed down into the recess 26 and snap firmly therein while the cut surfaces 72 lie pressed together in a sealing relationship. As the person skilled in this art will realize, a surgeon is able to insert a probe through the self-sealing opening 23 and plug 70, for instance plug according to FIG. 13, can then be pressed laterally on the probe immediately outside the cap or closure means 20. The plug is then compressed circumferentially and pressed axially down into the recess 26, so that the waist portion 74 of the plug snaps into the undercut 27. Radial compression of the plug reduces the size of the opening 71' so that the probe will be essentially fixated axially in the plug 70. This thus results in axial fixation of the probe to the instrument. The plug and the probe can, of course, be removed from the recess 26, by moving the rear parts of the plug 70 out from the cap 20 and gripping said parts manually.

As will be evident from FIG. 11, the front part 77 of the plug 70 is conical so as to facilitate its insertion through the inlet opening 28 to the recess 26. It will also be evident from FIG. 11 that the bottom part 26' of the recess 26 is conical and has a slightly larger cone angle than the front part of the plug 70, so as to ensure that the plug will provide an effective seal against axial leakage.

Different plugs 70 may be provided to enable rod-like elements of mutually different diameters to be fixed in the cap or end closure means 20 of the instrument. These rod-like elements will be effectively sealed axially by the plug, despite having a diameter which is smaller than the diameter of the self-sealing lead-through or transit 23.

The invention being thus described, it will be obvious that the same may be varied in many ways. Such variations are not to be regarded as a departure from the spirit and scope of the invention, and all such modifications as would be recognized by one skilled in the art are intended to be included within the scope of the following claims.

What is claimed is:

1. An instrument for use in uterine laparoscopic surgery, said instrument comprising a tubular element defining an interior passageway and having a front end-part for receiving the cervix and a rear end-part, said front end-part including an edge portion having a curvature by which the top wall of the vagina is supported around a periphery of said edge portion when the tubular element is positioned in the vagina, and said rear end-part including an outer edge having a slit for anchoring a suture which is anchored through the cervix and passes through the passageway.

2. The instrument according to claim 1, further comprising end closure means, detachably fastened to the rear end-part of the tubular element, for pressure-sealing a passageway passing through an interior of said tubular element.

3. The instrument according to claim 1, wherein the edge portion of the tubular element includes a single-curved surface whose concave side lies distal from the tubular element, a generatrix of the single-curved surface being perpendicular to a longitudinal axis of the tubular element, and a plane which approximates the single-curved surface and which extends parallel with said generatrix defines an angle of roughly 30° with a plane extending normal to the longitudinal axis of the tubular element.

4. The instrument according to claim 2, wherein the end closure means has a central, self-sealing lead-through for receiving a rod-shaped element inserted sealingly into the passageway of the tubular element.

5. The instrument according to claim 4, further comprising a clamping sleeve having a manipulator grip which is firmly clamped on the rear end-part of the tubular element.

6. The instrument according to claim 4, wherein the self-sealing lead-through in the end closure means is provided in a recess having an undercut part, a plug inserted into the recess having an enlarged peripheral part for snapping into the undercut part, the plug having a through-passing passageway which is aligned with the self-sealing lead-through, thereby enabling the rod-shaped element to be gripped in the through-passing passageway in the plug and fixated axially in said plug when said plug is pressed into the recess.

7. The instrument according to claim 6, wherein the plug has a lateral opening for enabling the rod-shaped element to be inserted laterally into and removed laterally from the through-passing passageway in said plug when the plug is located outside the recess.

8. The instrument according to claim 6, wherein at least one of the plug and a wall of the recess is comprised of a rubber elastic material.

9. The instrument according to claim 8, wherein the plug prevents axial leakage of fluid between the rod-shaped element and the recess wall.

10. An instrument for use in uterine laparoscopic surgery, said instrument including a tubular element having a central passageway, a front end-part for insertion into the vagina and for receiving the cervix, and a rear end-part, an edge portion of the front end-part of said tubular element shaped to support against a top wall of the vagina, a sealing ring embracing the tubular element and providing a seal between said element and the vaginal wall said edge portion of the front end-part of the tubular element having a curvature by which the top wall of the vagina is supported when the tubular element is positioned in the vagina, and an end closure means detachably fastened to the tubular element, said rear end-part of the tubular element having anchorage means for a suture which is anchored through the cervix and carrying said end closure means to pressure-seal the passageway passing through said tubular element.

11. The instrument according to claim 10, wherein said rear end-part of the tubular element includes a wedge-shaped slit in which a suture can be anchored.

12. The instrument according to claim 10, wherein the edge portion of the tubular element is defined by a section between the tubular element and a single-curved surface whose concave side lies distal from the tubular element a generatrix of the single-curved surface being perpendicular to a longitudinal axis of the tubular element, and a plane which approximates the single-curved surface and which extends parallel with said generatrix defines an angle of roughly 30° with a plane extending normal to the longitudinal axis of the tubular element.

13. The instrument according to claim 10, wherein the end closure means has a central, self-sealing lead-through which is adapted to enable a rod-shaped element to be inserted sealingly into the passageway of the tubular element.

14. The instrument according to claim 13, wherein the end closure means has a tubular flange which embraces the rear end-part of the tubular element, a clamping sleeve which includes a manipulator grip being firmly clamped on the rear end-part of the tubular element.

15. The instrument according to claim 14, wherein the clamping sleeve includes a rod which can be connected to an external attachment point.

16. The instrument according to claim 13, wherein the self-sealing lead-through in the end closure means is provided at a bottom of a recess that extends towards the interior passageway of the tubular element, the recess having an undercut part such that a plug can be inserted into the recess and an enlarged peripheral part of the plug snaps into the undercut part, the plug having a through-passing passageway which is aligned with the self-sealing lead-through, therewith enabling a rod-shaped element to be gripped in the through-passing passageway in the plug and fixated axially in said plug when said plug is pressed into the recess.

17. The instrument according to claim 16, wherein the plug has a lateral opening for enabling the rod-shaped element to be inserted laterally into and removed laterally from the through-passing passageway in said plug when the plug is located outside the recess.

18. The instrument according to claim 16, wherein at least one of the plug and a wall of the recess is comprised of a rubber elastic material and an insertion end of the plug is conical the bottom part of the recess also being conical and having a slightly larger cone angle than the plug insertion end, a cone-apex part of the plug being compressed more pronouncedly circumferentially around a rod-shaped element in said plug through-passing, passageway in coaction with the bottom part of the recess wall.

19. The instrument according to claim 16, wherein the plug prevents axial leakage of fluid between the rod-shaped element and a wall of the recess in coaction with a wall of the recess.

* * * * *